United States Patent
Prusik et al.

(10) Patent No.: US 7,019,171 B1
(45) Date of Patent: Mar. 28, 2006

(54) PARTICLE SIZE CONTROL FOR ACETYLENIC AGENTS USEFUL IN CONDITION MONITORING SYSTEMS

(75) Inventors: Thaddeus Prusik, Stroudsburg, PA (US); Dawn Smith, Martinsville, NJ (US); Ingo Leubner, Penfield, NY (US)

(73) Assignee: Temptime Corporation, Morris Plains, NJ (US)

( * ) Notice: Subject to any disclaimer, the term of this patent is extended or adjusted under 35 U.S.C. 154(b) by 50 days.

(21) Appl. No.: 11/002,818

(22) Filed: Dec. 2, 2004

(51) Int. Cl.
*C07C 273/18* (2006.01)

(52) U.S. Cl. ..................................... 564/61
(58) Field of Classification Search ............... 564/61
See application file for complete search history.

(56) References Cited

U.S. PATENT DOCUMENTS

| | | |
|---|---|---|
| 3,999,946 A | 12/1976 | Patel et al. |
| 4,189,399 A | 2/1980 | Patel |
| 4,384,980 A | 5/1983 | Patel |
| 4,788,151 A | 11/1988 | Preziosi et al. |
| 4,789,637 A | 12/1988 | Preziosi et al. |
| 5,902,899 A * | 5/1999 | Hayashi et al. ............... 564/58 |

OTHER PUBLICATIONS

U.S. Appl. No. 10/900,448, filed Jul. 28, 2004, Prusik et al.
I.H. Leubner, *Journal of Crystal Growth 84, Crystal Formation (Nucleation) in the Presence of Growth Restrainers*, p. 496-502. (1987).
Ingo H. Leubner, *The Journal of Physical Chemistry vol. 91, No. 23. Crystal Formation (Nucleation) under Kinetically Controlled and Diffusion-Controlled Growth Conditions*, p. 6069-6073. (1987).
*FBRM: Focused Beam Reflectance Measurement* Data Sheet As downloaded from www.lasentec.com on Mar. 1, 2005.
*FBRM Models* Data Sheet As downloaded from www.lasentec.com on Mar. 1, 2005.
*FBRM Brief Method of Measurement* Data Sheet As downloaded from www.lasentec.com on Mar. 1, 2005.
*Disperbyk-2050* Data Sheet As downloaded from www.byk-chemie.de on Oct. 14, 2004.
*Triton X-114 pure* Data Sheet As downloaded from www.serva.de on Oct. 14, 2004.

\* cited by examiner

*Primary Examiner*—Peter O'Sullivan
(74) *Attorney, Agent, or Firm*—Kirkpatrick & Lockhart Nicholson Graham LLP

(57) ABSTRACT

Precipitation of polyacetylenic agents can be effected with control of a particle size parameter such as mean size or spread, by mixing a warm solution of the acetylenic agent with a cold precipitation fluid and appropriate selection of a constituent of the cold precipitation fluid and/or of the temperature conditions and collecting the precipitated acetylenic agent. Precipitation additives such as nitrocellulose or gelatin can usefully be employed. Solvents such as aqueous methanol and ethyl 3-ethoxypropionate can be useful. Polyacetylenic agents, e.g. substituted diacetylenics are useful to provide visual changes in condition-monitoring indicators such as time-temperature indicators, "TTIs", useful as freshness indicators for radiation exposure monitoring and for other purposes. Controlled, small and/or consistent particle sizes of such polyacetylenic agents are helpful in providing consistent commercial properties, especially in inks in which they may be formulated.

29 Claims, No Drawings

PARTICLE SIZE CONTROL FOR ACETYLENIC AGENTS USEFUL IN CONDITION MONITORING SYSTEMS

STATEMENT REGARDING FEDERALLY SPONSORED RESEARCH OR DEVELOPMENT (Not applicable.)

BACKGROUND OF THE INVENTION

The present invention relates to processes for preparing acetylenic active agents, useful in compositions for monitoring and providing a cumulative indication of exposure to certain deleterious ambient conditions. The invention also relates to systems, elements, components, and compositions incorporating such acetylenic agents and to indicators and other devices in which such compositions may be incorporated.

In particular, but without limitation, the invention relates to such compositions and the like which are useful for monitoring conditions to which an associated host product, for example, a foodstuff, a vaccine or a medication, has been exposed, including the elapse of a predetermined integral of deleterious ambient conditions which can correlate with the shelf life of such a product especially an integral of temperature over time. Such time-temperature indicators are referenced "TTI" herein. The elapse of a predetermined parameter or combination of parameters, for example time and temperature, can be indicated by a change in color or other visual characteristic.

Acetylenic agents including substituted diacetylenics and others are well known for use in shelf life monitoring systems. In general, as described in, for example, Patel et al. U.S. Pat. No. 3,999,946, acetylenic agents useful in the invention comprise polyacetylenic compounds having two or more conjugated acetylenic groups (—C≡C—C≡C—). These reactive groups cause the acetylenic active agents to polymerize, providing a distinct visual change, under many commonly encountered conditions of time and temperature and other environmental parameters. As taught by Patel et al. '946, useful acetylenic compounds may be monomeric or polymeric, cyclic or acyclic, provided that they contain at least two conjugated acetylenic groups. Examples of suitable acetylenic compounds include diynes, triynes, tetraynes and hexaynes. Patel et al. '946 disclose the synthesis of many diacetylenic monomers and other useful diacetylenic agents and their incorporation into TTIs and other shelf life indicator compositions where they may provide a cumulative indication of temperature fluctuations over time. Individual acetylenic agents may be selected, or tailored to specific applications, with varying degrees of difficulty to provide active agents with particular desired time-temperature or other condition-indicating characteristics. Such diacetylenic compounds and agents are generally suitable for the purposes of the present invention and are referenced herein as "acetylenic agents".

Acetylenic agents useful for the purposes of the invention are sometimes described in the art, with more or less precision, as "monomers", "diacetylenic monomers", or "substituted diacetylenic monomers". All such diacetylenic materials that can provide a detectable indication of exposure to an environmental condition, optionally on a cumulative basis, are to be understood to be embraced by the term "diacetylenic agent" as it us used herein.

Patel U.S. Pat. Nos. 4,189,399 and 4,384,980 and Preziosi et al. U.S. Pat. Nos. 4,789,637 and 4,788,151 provide examples of other acetylenic agents useful in shelf life systems, including modifications of such agents, broad ranges of substituents that may be made and complexes in which they may be incorporated, as well as methods of synthesis and blending, for example in co-crystallization operations that are known to the art and which may be employed in the practice of the present invention. The disclosure of each one of the aforementioned Patel and Preziosi patents is hereby incorporated herein by this specific reference thereto.

Condition-indicating acetylenic agents such as those described above have physico-chemical properties that are particularly useful for the purposes of the invention, for example an ability to polymerize in response to persistent temperature excursions and to transform into colored solid state reaction products which contrast strikingly with the starting material. Conditions monitored may include time, temperature, humidity, actinic radiation, vaporous atmosphere, and the like, to which an associated host product, for example a foodstuff, vaccine or medicament, or host organism, has been exposed, as well as combinations of two or more of the foregoing conditions.

Generally, acetylenic agents useful in the practice of the invention can give a distinct visual indication, such as a change of color hue or of color density, of the elapse of a predetermined time-temperature integral which may be selected to flag the expiration of the shelf life of the associated host product.

Conveniently the acetylenic agent may be embodied in a product label affixed to a perishable or freshness-sensitive host product, for example a foodstuff or a medicament or the like, which product is known to be adversely affected by, for example, excessive thermal exposure.

Usefully, especially for inclusion as an element of a product label, the acetylenic agent is incorporated into a composition formulated as a printable ink. The resultant printable ink may be applied in a suitable pattern to a label, wrapper or wrapping component, which can be associated, by adhesive layer or other means, with a target product having a limited shelf life, for example, an item of foodstuff or medicament. Desirably, at the expiration of a predetermined period, the applied TTI ink label composition displays a predesignated color or color density, signaling expiration of the product's shelf life. A reference mark may be provided closely adjacent to the TTI to facilitate visual determination of the predesignated color or color density.

It should be noted that although the term "monomer" is sometimes used to denote active acetylenic monitor component materials intended to be employed in TTIs, dimeric and polymeric component compounds derived from a similar basic structure, for example as described in the above-mentioned references, can also be employed. The term "acetylenic agent" as used herein is intended to embrace various such reactive diacetylenic compounds that are capable of polymerizing in response to conditions of interest while providing a useful detectable parameter change, notably, but not exclusively, a distinct visual change. Other parameters, for example electrical parameters such as conductivity dielectric constant, or the like might be detected, if desired, and the invention can also employ reactive acetylenic agents capable of providing such other changes in response to relevant parameter changes.

As is known from the above-referenced patents, and other documents, numerous diacetylenic monomers and other useful acetylenic agents may be synthesized to yield TTI components of widely varying reactive temperature ranges and resultant color densities. Such acetylenic agents have long been employed to provide useful, reproducible results as indicators of shelf life end points, with largely satisfactory results.

Of considerable significance with regard to the above-described TTI technology is that, once the acetylenic agents have been synthesized and recovered, it is usually desirable to store them at relatively low temperatures, for example, below about 4° C. to inhibit premature polymerization. Also, further downstream processing operations, including application to a host product, are desirably performed at low temperature. Furthermore, even with careful storage, active acetylenic agents have relatively short shelf lives, as compared with other industrial fine chemicals normally stored at room temperature. The need for low-temperature storage impacts most aspects of the subsequent handling, processing and marketing of condition-indicating acetylenic agents and products incorporating them.

Generally, the acetylenic agents once synthesized are recovered in the solid state by precipitation as crystals from solution. For many purposes it is desirable that crystallization be performed rapidly to yield relatively small crystals or other particles. However, at least some of the precipitated particles conventionally obtained may be undesirably large, especially for applications calling for the acetylenic agent to be formulated into an ink for printing or marking on a label or other substrate. Accordingly, it is a common practice in the art to grind, pulverize, mill or otherwise mechanically comminute the raw acetylenic agent crystals to obtain a particulate product having desired size characteristics, for example characteristics rendering the acetylenic agent particles suitable for use in a free-flowing ink that may be effectively applied to a printed label, tag, product wrapper component or the like.

One drawback of mechanical comminution is that it adds a relatively costly step or steps to the overall process. Furthermore, the mechanical action adds heat to the sample and may cause unwanted color development. Another drawback is that the quality of the inks produced may be inconsistent or sometimes unsatisfactory. It would therefore be desirable to provide a method of preparing particulate condition-indicating acetylenic agents which yields acetylenic agents in particulate or crystallized form that are well suited for use in TTI inks, and which avoids mechanical comminution.

Furthermore, to reduce inconsistencies in the printing of TTI indicators, pursuant to the invention it is now understood that it would be desirable to limit the presence of oversized particles in the particulate acetylenic agents.

In an unrelated art, I. H. Leubner, in a research paper regarding laboratory experimentation published in J. Crystal Growth, 84: 496 (1987), '*Crystal Formation (Nucleation) in the Presence of Growth Restrainers* reports that when certain compounds are present during nucleation in silver halide precipitation, more and thus smaller crystals are obtained than in their absence (abstract). Specifically, Leubner added silver nitrate and halide solutions simultaneously to a stirred 4% gelatin solution. A mercapto-tetrazole restrainer, namely 2-(3-acetamidophenyl)mercapto-tetrazole, at concentrations of from 0-(500 mg/l (0–0.05% by weight), was added to the gelatin solution (Table 1). Reported precipitating silver halide crystal sizes were progressively reduced at different concentrations from about 0.4 micron without restrainer to about 0.14 micron with 500 mg/l restrainer. A number of theoretical considerations are described to explain the results, and a mathematical model of the restrainer effect is described. The model is contemplated by Leubner as being generally applicable to describe the growth effects of restrainers on crystals. However, nothing in Leubner's data, limited as it is to the specialist photographic-related field of silver-halide-in-gelatin precipitation, provides a commercially convincing suggestion that Leubner's tetraazole restrainer would be effective to control particle size in other systems. Thus, the TTI acetylenic agents employed in the practice of the present invention are not at all like Leubner's silver halide. Furthermore, the acetylenic agent crystallization processes to which the present invention relates, which are frequently recrystallizations, are quite different from Leubner's process of in situ synthesis and precipitation of silver halide into a gelatin-rich, viscous medium. Leubner's academic theories do not appear germane to the practical commercial problems addressed by the present invention.

Accordingly, there is a need for a non-comminutive process for favorably influencing particle size in acetylenic agent crystallization processes.

The foregoing description of background art may include insights, discoveries, understandings or disclosures, or associations together of disclosures, that were not known to the relevant art prior to the present invention but which were provided by the invention. Some such contributions of the invention may have been specifically pointed out herein, whereas other such contributions of the invention will be apparent from their context. Merely because a document may have been cited here, no admission is made that the field of the document, which may be quite different from that of the invention, is analogous to the field or fields of the present invention.

SUMMARY OF THE INVENTION

It is an object of the present invention to provide a method of preparing particulate, condition-indicating acetylenic agents with desirable size characteristics without employing mechanical comminution.

Another object is to provide a method of preparing particulate, condition-indicating acetylenic agents which acetylenic agents are well suited to be formulated into inks that are capable of consistently good performance in printing TTIs.

To fulfill these and other objects, the present invention provides a process for recovering an acetylenic active agent from solution, the process comprising:
 a) precipitating the acetylenic active agent by mixing a warm solution of the acetylenic agent with a cold precipitation fluid to precipitate the diacetylenic agent from the resultant mixture;
 b) controlling at least one size parameter of the precipitated diacetylenic agent by selection of at least one constituent of the cold precipitation fluid; and
 c) collecting the precipitated diacetylenic agent.

It will be understood that the warm solution of acetylenic agent may be prepared by dissolving solid crystals or powdered acetylenic agent in a suitable solvent, by reconstituting a cake, slurry or other semi-solid mass of acetylenic agent in the solvent, by synthesizing the acetylenic agent in situ in the solvent, or in other suitable manner.

The precipitated acetylenic agent can be largely or entirely crystalline, comprising for example at least 90 or 99% crystals, the balance of precipitated acetylenic agent, if any, comprising amorphous particles.

The invention includes the collected precipitated diacetylenic agent as well as inks and other products formulated from the precipitated diacetylenic agent and TTIs made from the inks or from such other products.

The method of the invention comprises a number of useful embodiments for effecting control of a size parameter during recrystallization of the active acetylenic agent. These embodiments include appropriate selection of at least one constituent of the cold precipitation fluid. For example a novel precipitation fluid may be selected. Alternatively, or in addition, a solvent-soluble precipitation additive may be selected and incorporated in the precipitation fluid. If desired, the concentration of the precipitation additive in the solvent may be selected to foster a desired particle size characteristic. Embodiments of the invention also include selection of the solvent, selection of the precipitation additive and, optionally, of the additive's concentration to promote the obtaining of one or more desired size characteristics.

The size parameter controlled can be that the acetylenic agent particles are desirably small, not exceeding a certain mean particle size or are substantially free of certain rather large particles being particles of a specified size somewhat greater than the mean particle size, examples of which are further described hereinbelow. Consistency and repeatability of performance in the printing or other TTI manufacturing process is desirable and such consistency is believed fostered by employing the methods of the invention which can be repeated to provide particle size distributions which have a desired character and consistent characteristics from one production batch to the next.

In one embodiment of the inventive method, which may be employed alone or in conjunction with other embodiments, the controlling of at least one size parameter of the precipitated diacetylenic agent comprises managing the temperatures of the acetylenic agent solution and the recrystallization mixture to facilitate production of acetylenic crystals having a desirable size parameter.

By taking active measures to determine that the precipitated diacetylenic agent has desirable size characteristics, which measures avoid mechanical comminution or other heat generation steps, the invention enables a better product to be provided improving the quality and performance of inks and other products formulated from precipitated diacetylenic agents.

DETAILED DESCRIPTION OF THE INVENTION

The present invention relates to processes for precipitation of active acetylenic agents from a solution, usually a warm solution, which solution may have been prepared by redissolution, in situ synthesis or other suitable means. Commonly, the acetylenic agent precipitate will be crystalline. However it is conceivable that in some cases the precipitate may largely comprise, or may include, amorphous particles. In the following description reference will be made to crystallization or recrystallization with the understanding, that unless the context suggests or implies otherwise, precipitation of amorphous particles is intended to be included, if appropriate.

Thus, some useful crystallization processes to which the invention relates typically comprise batch cooling of an acetylenic agent solution from a solution temperature of about 90 to 100° C. to a temperature below the crystallization point of the acetylenic compound. Usually, but not necessarily, the crystallization process is a recrystallization wherein the acetylenic agent solution is prepared by dissolving acetylenic agent crystals. However, the processes of the invention could be applied to crude reaction product solutions or concentrates of acetylenic agents, if desired.

Cooling may be effected by overall cooling, for example by immersion of the solution vessel in an external bath of coolant, or by quenching by rapid introduction of the acetylenic agent solution directly into a body of a cooler quenching fluid which functions as a precipitation medium. Often, a significant portion of such conventionally recrystallized acetylenic agent product has a mean particle size well in excess of a desirable size for compounding into shelf life monitoring system compositions, such as inks for printed labels or the like. An acetylenic agent precipitated with or without quenching is normally recovered, after washing, filtration, and drying, as a crystalline product which exhibits a wide range of particle sizes, comprising both individual and agglomerate particles.

Thus, stock acetylenic agent products of such methods may have fragmented and agglomerated particles with a distribution of sizes in a range which in some cases may be as high as from about 40 µm to about 80 µm. More commonly, conventionally made acetylenic agents such as 2,4-hexadiyn-1,6-bis (ethylurea), also known as "KE monomer", typically have a mean particle size of about 17–23 micron, and co-crystallized acetylenic agents, such as co-crystallized mixtures of the KE monomer and 2,4-hexadiyn-1,6-bis (propylurea) (also known as "KPr monomer"), the mixture also being known as a "KX monomer" have a mean particle size of about 18–38 micron. These size ranges are based upon merely exemplary of the order of magnitude of typical conventional commercially available acetylenic agent crystals. As may be understood from the foregoing discussion, such crystal sizes may be too great for some purposes, notably for incorporation in printing inks. For printing ink formulation, mean particle sizes of 15 µm or less, for example 12 µm or even 10 µm or less, would be desirable and the invention includes acetylenic agents meeting such size criteria.

Prior to the present invention it has been a practice to reduce the recrystallized acetylenic agent particle size for use in TTI ink compositions in a mechanical comminution operation, typically by pulverizing or milling the ink composition with rollers, balls, high-speed shearing or other apparatus. While useful size reduction may be achieved by these means the results still may not be entirely satisfactory and significant undesirable variation in TTI composition may result. Pursuant to the present invention it has been determined that after mechanical comminution the distribution of acetylenic agent particle sizes may span an undesirably wide range leading to end product inconsistencies. It may be understood, in light of the invention, that unduly large particles may be problematic in some printing processes, for example in silk screen printing process where the ink must pass through a fine-meshed screening element.

A further disadvantage of milling or grinding operations, is that the mechanical force applied to the particles causes heat generation, which may result in premature color-shift polymerization of some acetylenic agent materials or of some particles in a batch of material. It will be apparent that reactive acetylenic materials capable of monitoring temperature conditions may well be sensitive to localized heat generation during processing.

The added cost is also a drawback of mechanical comminution. A still further problem, as understood by the present invention, is that the control of the size parameters achieved by mechanical comminution may also be poor. The particles produced may have an excessively wide range of particle sizes leading to poor quality inks. It is also contemplated, pursuant to the invention, that variations or irregularities in the size or size distribution of the crystalline particles of acetylenic agent may have a significant effect upon the response and performance of the agents when they are employed in TTI or other monitoring applications. In particular, as suggested above, the presence of small quantities of relatively large particles may adversely affect printing performance.

The present invention has embodiments that solve these problems by actively taking suitable measures to control at least one particle size parameter, such as a mean size dimension, or the presence of particles of an undesired size, during crystallization of the acetylenic agent. As is more fully described elsewhere herein, size parameter control can be effected by utilizing a precipitation medium to effect crystallization, by optionally also using a precipitation additive and by suitable selection of the materials of the precipitation system and their concentrations.

As is described and claimed in copending, commonly owned U.S. patent application Ser. No. 10/900,448 filed Jul. 28, 2004, entitled "MORPHOLOGY CONTROL OF SUBSTITUTED DIACETYLENIC MONOMERS FOR SHELF LIFE MONITORING SYSTEMS" of Prusik et al. (referenced "the copending application" hereinafter), the entire disclosure of which is hereby incorporated herein by reference thereto, a useful control of at least one acetylenic agent particle size parameter can be obtained, without resort to deleterious grinding, by quenching a heated solution of the acetylenic agent with a cold quenching fluid, employing certain temperature controls. As disclosed in the copending application, quenching is carried out in such a manner as to effect and maintain a substantial and rapid temperature decrease of the resulting fluid crystallization mixture. Such temperature control measures can be employed in the practice of the present invention, if desired.

Pursuant to the present invention, crystal size control of the acetylenic agent may comprise control of one or more size parameters such as the mean particle size, the exclusion or avoidance of particles above a size threshold, the spread of the particle size distribution, as indicated for example by a decade ratio, the size parameters of a particular fraction, for example the first decile, or the tenth decile of a sized sample, or other desired size-related parameter. By actively controlling at least one size parameter, rather than relying upon conventional methods of recrystallization which yield products which in light of the present invention can be seen to have less than desirable size characteristics, improved manufacturing consistency and other benefits can be obtained.

The process may be controlled to have a desired outcome, for example to yield size characteristics meeting one or more size criteria. There are of course a number of different ways of measuring particle size and these ways may give more or less different results. Conventional particle sizes referenced herein may be understood to be approximate figures as may be determined by traditional light scattering methods employing, for example, a Horiba® LA-910 instrument.

However, as used hereinbelow, when describing experimental results, and useful particle size criteria, the particle size measurements given reference the mean chord size, as determined by the Lasentec® FBRM method which is further described hereinbelow. In some cases Lasentec® mean chord size figures may be about 20% smaller than mean diameter figures obtained by light scattering, the degree of difference being influenced by particle shape, as will be understood by those skilled in the art.

The size parameter controlled can comprise an average particle size or a particle size distribution parameter or both a particle size and a particle distribution parameter. Alternatively, or in addition, the size criterion may be that essentially no particles, or only a very small proportion, such as 1 percent, 0.1 percent or 0.01 percent by weight, exceed a certain threshold size of, for example 100 μm, more desirably, 50 μm or possibly of about 30 μm, referring to a Lasentec®-determined mean chord size.

All proportions of ingredients in this description are on a weight basis, unless otherwise specified or apparent from the context.

Pursuant to the invention, useful size criteria include a mean particle size of not more than about 15 micron (also referenced as "μm" herein), and a mean particle size lying within the range of from about 5 μm to about 10 μm. Other useful mean particle size criteria may be known to those skilled in the art or can be determined by routine experimentation.

Other useful size criteria that may be employed in practicing useful embodiments of the invention include sample or fractional size measurements, such as particular values or ranges for $C_{10}$, $C_{50}$, and $C_{90}$ fractions, or ratios of such fractions or samples, for example the decade ratio. These fractions, or ratios may be determined by Lasentec® methods and are described in more detail hereinbelow. Thus, some useful size criteria, which may be employed, as alternatives to or in addition to mean particle size criteria, include a $C_{90}$ fraction not in excess of about 35 μm, or usefully, not in excess of 25 μm and a decade ratio not exceeding 15, or usefully, not exceeding 12.

As described above embodiments of the inventive process can yield relatively small particle size acetylenic agents useful for time-related condition-sensing which particles also have a desirable size distribution, without grinding milling or other mechanical comminution operations. However, it will be understood that loose agglomerations of particles that may be present and which constitute oversized masses, may be broken up or dispersed by low-stress mechanical operations, if desired, or by other suitable means such as repeated washing.

The crystallization process of the invention includes useful embodiments wherein the acetylenic agent average particle size or particle size distribution is controlled by the presence of a dissolved precipitation additive material to provide a recoverable crystal product which is suitable for use in an ink. Some useful embodiments provide a free-flowing ink of good quality, without need for, or with a reduced need for, mechanical treatment to comminute overly large particles. Thus the expense, and other drawbacks of milling or grinding may be avoided while still providing satisfactory condition-indicating inks.

The crystallization process of the invention will now be described in more detail referring initially to conventional aspects of the process.

Acetylenic Agents. Substituted diacetylenic monomers, or other acetylenic agents, of predetermined time-temperature integral selected for a particular application, for example for use in the preparation of a shelf-life monitoring system, for instance a TTI device, may be synthesized as described in the above-referenced United States patents and elsewhere in the art. For example, synthesis may be effected by appropriate selection and balance of various parameters, such as precursor acetylenic condensate constituents or substituted variants thereof, conditions of synthesis, matching of components for co-crystallized compositions, and the like. The resulting compound is then initially recovered from the reactant solution by known crystallization methods, such as evaporation, sublimation, solution cooling, or selective dissolution, as a crude, crystalline acetylenic product. Some specific examples of such substituted diacetylenic agents which can be so manufactured and are useful in the practice of the present invention, include, without limitation: 2,4-hexadiyn-1,6-bis (ethylurea); 2,4-hexadiyn-1,6-bis (propylurea); and co-crystallization mixtures of 2,4-hexadiyn-1,6-bis (ethylurea) and 2,4-hexadiyn-1,6-bis (propylurea). Other diacetylenic agents which can be employed may be found in the above-cited patents or will be known to those skilled in the art and include other 2,4-hexadiyn-1,6-bis(alkylurea) compounds and co-crystallized mixtures thereof, such for example as butyl-, octyl-, dodecyl- and octyldecyl-substituted 2,4-hexadiyn-1,6-bis(alkylurea) with linear alkyl substituents and co-crystallization mixtures of any of the herein listed 2,4-hexadiyn-1,6-bis(alkylurea) compounds.

Solvents for the Acetylenic Agent. The crude crystalline acetylenic agent can be purified by dissolving it in, and recrystallizing it from, a suitable solvent for subsequent formulation into a TTI composition. Suitable solvents are known and include highly polar organic solvents, for example glacial acetic acid, propionic acid, dimethyl formamide ("DMF") and dimethyl sulfoxide. As is also known, useful condition-sensitive acetylenic agents are usually soluble in only a small number of solvents, sometimes exhibiting solubilities useful for processing only at elevated temperatures within, say, 20 to 40° C. of the reflux temperature. Some other solvents which may be employed or tried, to dissolve a particular acetylenic agent include: alkyl esters of a monocarboxylic acid; higher alkyl alcohols containing more than one carbon atom; an alkylated benzene; cyclic ethers; alkyl ketones; alkyl glycol ethers; halogenated alkyl hydrocarbons; ethyl acetate; methyl propionate; ethanol; butanol; isopropanol; toluene; xylene; trimethylbenzene; isopropylether; 1,2-dimethoxyethane; tetrahydrofuran; dioxane; acetone; methylethyl ketone; chloroform; dichloromethane, dimethyl sulfoxide pyridine or a mixture of any two or more of the foregoing solvents.

Precipitation Medium. Desirably, the precipitation medium employed for quenching the hot acetylenic agent solution is chosen to be substantially a non-solvent for the acetylenic agent at the temperatures encountered during the crystallization process and to be miscible with the acetylenic agent solution. Solubility of the acetylenic agent in the precipitation medium would of course be counter productive and desirably is less than about 5%, more desirably less than about 1% and for example about 0.1% or less at the temperature of the hot solution.

Methanol is one solvent which can be employed. However, some useful embodiments of the invention employ nonmethanolic precipitation liquids or liquids comprising a maximum of 30 or even 50 percent by weight methanol. if desired the balance may be water, another aqueous medium or other suitable solvent. Useful precipitation liquid embodiments also include aqueous mixtures of lower $C_2$–$C_6$ alkanols such as mixtures of ethanol, propanol or butanol with from about 30 to about 90 percent by weight water. Examples of some other useful precipitation liquids include ethyl 3-ethoxypropionate, dimethyl formamide which may be used alone or in mixtures with other solvents provided the mixture meets the criteria described herein for precipitation media.

Other organic liquids, including petroleum ethers and distillates, heptane or hexane, that are compatible with the process conditions and ingredients, can be employed, as will be apparent to those skilled in the art, provided that they are capable of dissolving any precipitation additive it may be desired to employ and can meet the above-described criteria of miscibility with the acetylenic agent solution without dissolving the agent itself. Preferred are biologically and environmentally "friendly" solvents that can be employed in commercial manufacturing of the products to which the invention relates without harmful side-effects upon production personnel, end users or the environment. As noted above, solvents such as dimethyl formamide desirably are not used as precipitation liquids with acetylenic agents they may dissolve.

Precipitation Additive. Pursuant to the invention it has been discovered that the incorporation into a precipitation medium for use in acetylenic agent crystallization or recrystallization, of a small amount of a suitable precipitation additive can control and may significantly reduce the particle size or particle size distribution of the recrystallized acetylenic agent. In some cases, it appears that the growth of large crystals may be restrained, in favor of the growth of smaller crystals. Suitable quantities to obtain a desired effect can be determined by routine experimentation and may, for example, be in the range of from about 0.001% to about 2% by weight of the precipitation medium with proportions of from about 0.005 to about 0.5% by weight being likely to be useful. Some useful embodiments can employ proportions of from about 0.05 to about 0.1% by weight. Excessive concentrations of precipitation additive may, in some cases cause agglomeration and therefore be undesirable. In some cases individual laboratory experiments may yield inconsistent or anomalous results. Accordingly, some routine experimentation to establish consistency may be desirable for implementation of commercial processes.

A precipitation additive, if employed in the processes of the invention, may be any suitable compound or material which helps control a size parameter, e.g. by limiting generation of overly large crystals, as is further described herein. Desirably, the precipitation additive is soluble or dispersible in the precipitation medium to provide a solution or dispersion, the dispersion, if utilized, preferably being a colloidal dispersion.

One illustrative class of precipitation additive compounds that may be employed or which may include useful and effective compounds, as may be determined by routine experimentation, comprises cellulosic esters or cellulose ether compounds. Useful cellulosic esters or cellulose ether compounds, optionally may contain electronegative groups including, by way of example, methyl, ethyl, and carboxymethyl cellulose, cellulose acetate, butyrate, propionate, cellulose acetate butyrate, and cellulose nitrate, more commonly called "nitrocellulose" compounds.

Nitrocellulose is one useful precipitation additive material, known to be useful in ink formulations comprising pulverized acetylenic agent shelf life monitoring compositions which has demonstrated compatibility with the functional monomers in such compositions. This compound can provide significant particle size restraining effect during recrystallization according to the present invention when included in precipitation medium solutions in amounts ranging from about 0.01% to 1.1%.

Other materials that may be useful as precipitation additives include other water-soluble polymers, surfactants, and the like and substances or complex materials that can wet the surfaces of the nascent crystals. Some examples of other materials that may be employed as precipitation additives include gelatin, substituted polyethylene glycol ethers such for example octylphenol polyethylene glycol ether available from Rohm and Haas under the trademark TRITON® X-114 and acrylate copolymers including the product available from Byk-Chemie AG under the trademark DISPERBYK®-2050. Suitable precipitation additives for a given precipitation may be determined, without undue experimentation, in light of the teaching herein.

While not being bound or limited by any particular theory, and with the objective of describing other crystal growth precipitation additives that may be employed or tested for employment in the methods and compositions of the present invention, it is believed that surfactants or polymers that are surface active under the recrystallization conditions may be useful as precipitation additives. Desirably, suitable precipitation additive compounds have adequate solubility to be dissolved in the precipitation medium at a concentration effective for crystal growth restraint.

To promote crystal quality, or for other desired purpose, ingredients other than those specified in the inventive processes described herein may be excluded, if desired. In other cases it will be understood that additional ingredients, co-crystallization active acetylenic agents, by-products or the like may be present as will be understood by those skilled in the art in the light of this disclosure.

Temperature Control. The hot acetylenic agent solution can be cooled in a variety of ways including unassisted cooling to room temperature and use of any one or more of various chiller means including, without limitation, an ice bath, dry ice bath and a programmable computer-controlled chiller. Employing these or other temperature control means, the temperature of the crystallization mixture can be controlled within desired limits to promote desired precipitate size characteristics. Suitable temperature conditions can furthermore be selected for ease of commercial implementation.

Desired temperature limits may include a reduction of temperature from the hot solution temperature of the acetylenic agent, e.g. from about 90 to about 110° C. to a temperature at least about 35° C. or more below the nominal acetylenic agent recrystallization temperature for the solvent, i.e. the temperature at which the acetylenic agent begins to crystallize from solution, which reduction of temperature is maintained throughout the crystallization process. Optionally, the lower temperature can be maintained within a narrow range, for example within a range of about 10 to 15° C.

Some other useful low temperature conditions for recrystallization include reduced temperature ranges of: from about −40 to about −35° C., from about −25 to about −15° C.; from about 3 to about 15° C.; from about 12 to about 48° C.; and from about 24 (or room temperature) to about 60° C. However, for commercial implementation, the invention recognizes that the lower, significantly sub-zero temperatures may be difficult or unduly costly to utilize and accordingly provides size-managing crystallization processes which can be effectively practiced at temperatures above −10° C., or even above 0° C. To this end, a temperature range of from about 0° C. to about 5° C. is contemplated as being commercially useful.

Some ways of practicing the present invention will now be illustrated by reference to the following examples. Although these examples reflect, as a matter of practicality, the use of a limited number of condition-indicating acetylenic agents, those skilled in the art will understand, in light of the teaching herein, that many other condition-indicating acetylenic agents can be employed and may become aware of other suitable acetylenic agents as the art develops.

EXAMPLE 1

(I) Preparation of Stock Acetylenic Compound (Gradual Cooling)

For use in subsequent examples, a stock composition of a monomeric substituted diacetylenic compound, 2,4-hexadiyn-1,6-bis (ethylurea), is prepared in a synthesis comprising the reaction of mono-propargylamine and ethylisocyanate as described for example in Example A of the above-cited Preziosi et al. U.S. Pat. No. 4,788,151. In a final stage of the synthesis process, the initial crystalline 2,4-hexadiyn-1,6-bis (ethylurea) is recovered and purified from an acetic acid solution by cooling in a recrystallization vessel at a moderate rate in an external water bath from about 90° C. to about 20° C. In the course of the gradual cooling, a significant amount of recrystallized acetylenic agent product appears at about 45° C., a temperature which can be regarded as the "nominal" recrystallization temperature for this concentration of the acetylenic material.

The resultant recrystallized stock acetylenic compound, when examined by optical microscopy, exhibits complex crystalline structures with fragmented and agglomerated particles having a broad estimated size distribution over a range of about 40 µm to 80 µm. Such microscopic examination may be useful for initial product comparisons and to assess aspects of morphology. However, a more reliable means for obtaining characteristic particle size specifications may be employed, including for example, Lasentec® Particle Sizer instrumentation which can provide automated statistical analysis and chord size specifications based on what are known as Focused Beam Reflection Method (FBRM) measurements.

In the following examples, acetylenic agent particle size characterizations specified as being by FBRM are made employing a Lasentec® FBRM model D600SX instrument. Lasentec analysis can be performed by dispersing powder samples in E3EP pursuant to the manufacturer's instructions, and sonicating for 15 minutes, if desired. Data obtainable and described herein includes a mean chord length which is a statistical average of all longitudinal and transverse axes of a particle, rather than a particle diameter which is obtained by more traditional methods such as light scattering, which methods assume the examined particles are spherical.

Also described are particle size distribution values for $C_{10}$, $C_{50}$, and $C_{90}$ fractions, indicating the maximum chord lengths for 10%, 50%, and 90% of the particles or, described another way, the chord length which embraces 10%, 50%, and 90% particles, respectively. In addition a $C_{90}/C_{10}$ decade ratio is described, being the ratio of the $C_{90}$ fraction to the $C_{10}$ fraction, sometimes referenced "DR" hereinbelow. References to a decade ratio hereinbelow are to be understood to be to the $C_{90}/C_{10}$ decade ratio, unless the context indicates otherwise. This decade ratio provides an indication of the range of particle size distribution or the spread of particle sizes in the sample. When characterized by these criteria, a sample of the foregoing stock monomer, 2,4-hexadiyn-1,6-bis (ethylurea), prepared by the gradual cooling method of Example 1 exhibits a particle size mean chord length of 24.4 µm, a $C_{10}$ of 3.4 µm, a $C_{50}$ of 16.7 µm, a $C_{90}$ of 51.5 µm and a $C_{90}/C_{10}$ decade ratio of 15.1.

COMPARATIVE EXAMPLE 2

Recrystallization of Co-Crystallized Mixture at −40 to −35° C. (No Additive)

A sample of a complex acetylenic agent comprising essentially a 2:1 co-crystallized mixture of 2,4-hexadiyn-1,6-bis (ethylurea) (sometimes referenced "KE monomer") and 2,4-hexadiyn-1,6-bis (propylurea) (sometimes referenced "KPr monomer"), prepared in the manner described for example in Example F of Preziosi et al. U.S. Pat. No. 4,788,151, hereinafter denoted as "the KX mixture", are recrystallized at low temperature utilizing an embodiment of the controlled-temperature quenching process described and claimed in the copending application. Specifically, in this example, about 300 parts of methanol precipitation medium are chilled to about − 40° C. in a stainless steel vessel in an acetone/dry ice bath, and about 35 parts of the KX mixture dissolved in 255 parts of acetic acid at 90° C. to provide an approximately 10.5% solution by weight, are introduced into the quenching vessel, with stirring, at a substantially constant rate of about 30 mL/min. The ratio of hot to cold liquids is about 1:1.05. The temperature of the resultant crystallization mixture is maintained to be not more than about −35° C. during the quenching and crystallization process.

EXAMPLE 3

Recrystallization of Co-Crystallized Acetylenic Agent Mixture at −40 to −35° C. with Precipitation Additive Comparative Example 2 is repeated with the difference that 0.1% by weight of nitrocellulose, on a dry weight basis, as a precipitation additive, is dissolved in the methanol precipitation medium, the percentage being calculated on a dry weight basis per unit weight of precipitation medium. The nitrocellulose employed is available from Gotham Ink under product NC-2513 and is described as having a mid-range viscosity and mid-range nitrogen content. This Gotham Ink product is intended to be used in the following examples where reference is made to employing nitrocellulose. As supplied, according to the manufacturer, the nitrocellulose is dissolved in a solvent mixture of isopropanol and ethyl 3-ethoxy propionate in an approximate proportion of 35:10:55 respectively, by weight.

COMPARATIVE EXAMPLE 4

Constant Rate Chilling of Co-Crystallized Acetylenic Agent Complex to 24° C.

Comparative Example 2 is repeated with the difference that cooling is effected under conditions mimicking a commercial manufacturing procedure for the KX mixture employing a glass beaker rather than a stainless steel vessel. The solution is held at 90–95° C. to ensure that the KX mixture is fully dissolved, and then is chilled to about 70° C. Over the following hour the temperature is brought down to 24° C. at a constant rate using a pre-programmed chiller, during which time the KX mixture crystallizes at a relatively slow rate compared to that in Example 2 and other examples in which the crystallization is forced by rapid quenching.

For each of Examples 24, the recrystallized KX mixture is recovered and characterized by FBRM analysis. Some results are described in Table 1 below.

COMPARATIVE EXAMPLE 5

Temperature-Controlled Crystallization of KE Agent

About six parts of methanol precipitation medium in which no precipitation additive is dissolved, are cooled in a polyethylene vessel to about 0° C. in an agitated ice-water bath having a temperature of about 0° C. A first aliquot of about one part of a 10.5% solution of 2,4-hexadiyn-1,6-bis (ethylurea), also referenced "the KE agent" herein) dissolved in 90° C. acetic acid (20 g KE in 170 g acetic acid) prepared by the method of Example 1, is mixed into the precipitation medium with stirring. The quenching mixture increases in temperature to about 10° C. before returning in a short time to the 0° C. base temperature, during which time significant formation of KE acetylenic agent crystals can be observed. A second similar aliquot of KE acetylenic agent solution is then added to the quenching mixture, and the mixture is allowed to recover to the 0° C. base temperature. Four further similar aliquots of KE acetylenic agent solution are added in like manner, allowing intervening recovery of the base temperature, for a total of six aliquots. Quenching of the entire volume of KE acetylenic agent solution is effected while preventing the quenched mixture temperature from rising above about 15° C., an increment of no more than about 15° C. above the initial 0° C. base temperature of the quenching fluid. The recrystallized KE agent is recovered as a slurry and characterized by FBRM analysis, without drying. Some results are described in Table 1 below.

EXAMPLES 6–10

Controlled Quenching of the KE Agent with Precipitation Additive

Example 5 is repeated except that five different concentrations of nitrocellulose precipitation additive are dissolved in the methanol quenching fluid. The proportion of nitrocellulose precipitation additive in each run and some results obtained are also described in Table 1 below.

COMPARATIVE EXAMPLES 11–12

Low-Temperature Controlled Quenching

The temperature-controlled recrystallization procedure of Example 5 is repeated utilizing methanol as quenching fluid, without a particle size precipitation additive, in a glass quenching vessel and employing more severe chilling. A programmed chiller or refrigeration apparatus is employed to provide a base methanol precipitation medium temperature of about −25° C. (Ex. 11) or −15° C. (Ex. 12). Recrystallization of the KE acetylenic agent occurs during the six acetic acid solution additions. The quenching mixture temperature rise at each addition of the warm KE agent/acetic acid solution is held to about 10° C. or less so that the mixture temperature does not exceed about −15° C. or −5° C., respectively. The recrystallized KE agent is recovered and characterized by FBRM analysis. Some results, along with the concentration of precipitation additive employed are described in Table 1 below.

EXAMPLES 13–15

Low-Temperature KE Crystallization with Various Concentrations of Precipitation Additive Example 11 is repeated except that three different concentrations of nitrocellulose precipitation additive are dissolved in the methanol quenching fluid. The proportion of nitrocellulose in each run and some results obtainable are also described in Table 1 below.

agglomeration which may explain the larger particle sizes obtainable with Examples 9 and 10.

EXAMPLE 16

Low-Temperature Asymmetric Acetylenic Agent Crystallization with Various Concentrations of Precipitation Additive Example 2 is repeated in four runs employing, respectively, 0.01, 0.025, 0.05 and 0.1% by weight of nitrocellulose precipitation additive and a co-crystallized mixture of

TABLE 1

Effect of Precipitation Additive on Particle Size of Recrystallized Acetylenic Agent

| | Process Conditions | | Chord Length (microns)$^2$ | | | | Decade Ratio$^3$ |
|---|---|---|---|---|---|---|---|
| Experiment | Minimum to Maximum Temp. | Precipitation additive (Nitrocellulose) | Mean | $C_{10}$ | $C_{50}$ | $C_{90}$ | |
| Ex. 2 (KX) | −40 to −35° C. | None | 10.4 | 2.1 | 7.5 | 21.9 | 10.4 |
| Ex. 3 (KX) | −40 to −35° C. | 0.10% | 8.3 | 1.7 | 5.4 | 18.0 | 10.6 |
| Ex. 4 (KX) | 70° to 24° C. | None | 28.1 | 3.5 | 16.4 | 57.8 | 16.5 |
| Ex. 5 (KE) | 0 to 15° C. | None | 15.8 | 2.9 | 11.7 | 33.3 | 11.5 |
| Ex. 6 (KE) | 0 to 15° C. | 0.11% | 9.2 | 2.0 | 6.4 | 18.9 | 9.5 |
| Ex. 7 (KE) | 0 to 15° C. | 1.10% | 10.0 | 1.9 | 6.0 | 21.7 | 11.4 |
| Ex. 8 (KE) | 0 to 15° C. | 0.05% | 9.9 | 2.1 | 7.0 | 20.9 | 10.0 |
| Ex. 9 (KE) | 0 to 15° C. | 0.25% | 14.4 | 2.1 | 7.5 | 35.7 | 17.0 |
| Ex. 10 (KE) | 0 to 15° C. | 0.50% | 13.6 | 2.0 | 6.8 | 34.5 | 17.3 |
| Ex. 11 (KE) | −25 to −15° C. | None | 15.4 | 2.7 | 11.6 | 32.4 | 12.0 |
| Ex. 12 (KE) | −15 to −5° C. | None | 12.0 | 2.2 | 8.4 | 25.8 | 11.7 |
| Ex. 13 (KE) | −25 to −15° C. | 0.05% | 11.2 | 2.2 | 7.9 | 23.7 | 10.8 |
| Ex. 14 (KE) | −25 to −15° C. | 0.10% | 8.1 | 1.9 | 5.9 | 16.5 | 8.7 |
| Ex. 15 (KE) | −25 to −15° C. | 0.25% | 12.4 | 2.2 | 7.9 | 29.2 | 13.3 |

Referring to Table 1, Examples 24 show how temperature control alone can be effective to reduce the particle size of the recrystallized KX mixture. Comparing the results for Example 2 with those for control Example 4 it can be seen that deep cooling the precipitation medium and holding the quenched mixture at a low temperature during recrystallization yields substantially smaller particles, with a significantly narrower size distribution, than are obtainable by employing programmed cooling down to room temperature, about 24° C. Example 3 shows that the presence of 0.1% precipitation additive in the precipitation medium reduces the particle size even further, providing a distinct reduction of the mean particle size, and also of each of the $C_{10}$, $C_{50}$ and $C_{90}$ fractions.

Examples 5–15 in each of which the KE agent (2,4-hexadiyn-1,6-bis (ethylurea)) is employed, demonstrate how various concentrations of precipitation additive can reduce the mean particle size of the KE agent crystals.

In each of Examples 6–10 and 13–15, it can be seen that when a nitrocellulose precipitation additive is employed, the mean, the C10 and the C50 values are reduced compared to the respective control, carried out under the same conditions, namely Comparative Example 5 or 11. In Examples 6–8 and 13–14, nitrocellulose also decreased the C90 and decade ratio compared to the control. Nitrocellulose appears to reduce the extent of crystal growth, and therefore to act as a precipitation additive in this process. However, it is theorized, that higher levels of nitrocellulose may cause asymmetric synthesis comprising 2,4-hexadiyn-1-ethylurea-6-propylurea dissolved in the hot acetic acid. Comparable results are obtainable.

EXAMPLE 17

Low-Temperature KPr Crystallization with Various Concentrations of Precipitation Additive Example 6 is repeated employing 2,4-hexadiyn-1,6-bis (propylurea). Comparable results are obtainable.

COMPARATIVE EXAMPLE 18

Crystallization of KE Agent in Ethyl 3-Ethoxy Propionate ("E3EP"), without Temperature Control About 300 g of a precipitation medium consisting of ethyl 3-ethoxy propionate (referenced "E3EP" herein, in which no precipitation additive is dissolved, are maintained at room temperature, about 24° C. About 30 g of the KE agent dissolved in 255 g of 90° C. acetic acid prepared by the method of Example 1, are mixed into the precipitation medium in one shot at a rate of about 2.5 l/min, with stirring.

The crystallization mixture increases in temperature approximately to the temperature shown in Table 2, below. The recrystallized KE agent is recovered as a slurry and characterized by FBRM analysis, without drying. Some results are described in Table 2 below.

EXAMPLES 19–20

Crystallization of KE Agent without Temperature Control, Using a Precipitation Agent Comparative Example 18 is repeated employing respective concentrations of 0.1 and 1.0 percent by weight of an acrylate copolymer precipitation additive, namely the product available under the trademark DISPERBYK® 2050 from Byk-Chemie A.G. Some results obtainable with Examples 19–20 are also described in Table 2 below.

TABLE 2

Recrystallization of KE agent using Byk 2050 in E3EP as Precipitation Medium

| | Restrainer | | Temperature | Slurry Particle Size (microns) | | | | |
|---|---|---|---|---|---|---|---|---|
| Experiment | Type | Conc. | Range ° C. | Mean | $C_{10}$ | $C_{50}$ | $C_{90}$ | DR |
| Ex. 18 | None | — | 24 to 61 C. | 10.2 | 2.0 | 7.5 | 21.1 | 10.4 |
| Ex. 19 | DISPERBYK 2050 | 0.1% | 23 to 59 C. | 10.8 | 2.2 | 8.1 | 22.1 | 10.3 |
| Ex. 20 | DISPERBYK 2050 | 1% | 24 to 59 C. | 10.5 | 2.0 | 7.7 | 21.8 | 10.9 |

It may be seen from Table 2 that recrystallization of the KE agent employing a E3EP as the precipitation medium without external cooling provides consistently small particles with a low DR indicating a narrow size spread. The Byk 2050 additive has little effect on particle size when added to E3EP at concentrations of 0.1% and 1.0%.

COMPARATIVE EXAMPLE 21

Crystallization of KE Agent in Methanol without Temperature Control

Example 18 is repeated using methanol as the precipitation medium in place of ethyl 3-ethoxy propionate ("E3EP"). Some results are described in Table 3 below.

EXAMPLES 22–23

Crystallization of KE Agent in Methanol without Temperature Control, Using PEG Ether Precipitation Agent Comparative Example 21 is repeated employing respective concentrations of 0.1 and 1.0 percent by weight of a precipitation additive consisting of a polyethylene glycol (commonly abbreviated as "PEG") ether, namely an octylphenol PEG ether available from Rohm and Haas under the trademark TRITON®, the product coded X-114 being employed. Some results obtainable with Examples 21–23 are also described in Table 3 below.

It may be seen from Table 3 that recrystallization of the KE agent employing methanol as the sole ingredient of the precipitation medium, without external cooling provides particles of an intermediate size with a moderate DR, indicating a moderate size spread. The TRITON® X-114 additive has little effect on particle size 21 when added to methanol at a concentration of 0.1% and significantly increases the 22 mean particle size and the size spread at a concentration of 1.0%.

EXAMPLE 24

Crystallization of KE Agent in Water/Methanol with Modest Temperature Control Example 18 is repeated using an 80/20 weight for weight mixture of water and methanol as the precipitation medium in place of ethyl 3-ethoxy propionate ("E3EP") and an ice bath to control the temperature to be within the range of about 3 to about 15° C. Some results obtainable are described in Table 4 below.

EXAMPLE 25

Crystallization of KE Agent in Water/Methanol with Modest Temperature Control, Using Gelatin as a Precipitation Agent Example 24 is repeated employing a concentration of 1.0 percent by weight of a precipitation additive consisting of gelatin of the type known as 225 bloom from calf skin, available from Aldrich Chemical Company. Some results obtainable with Examples 24–25 are also described in Table 4 below.

TABLE 3

Recrystallization of KE agent using Triton X-114 in Methanol as Precipitation Medium

| | Restrainer | | Temperature | Slurry Particle Size (microns) | | | | |
|---|---|---|---|---|---|---|---|---|
| Experiment | Type | Conc. | Range ° C. | Mean | $C_{10}$ | $C_{50}$ | $C_{90}$ | DR |
| Ex. 21 | None | — | 12 to 48 C. | 15.6 | 2.5 | 10.3 | 34.6 | 13.8 |
| Ex. 22 | Triton X114 | 0.1% | 12 to 48 C. | 15.5 | 2.5 | 10.2 | 34.5 | 13.8 |
| Ex. 23 | Triton X114 | 1% | 12 to 47 C. | 25.9 | 3.1 | 16.9 | 56.8 | 18.6 |

TABLE 4

Recrystallization of KE agent using Gelatin in 20% Methanol/80% Water as Precipitation Medium

| Experiment | Restrainer | | Temperature | Slurry Particle Size (microns) | | | | |
|---|---|---|---|---|---|---|---|---|
| | Type | Conc. | Range ° C. | Mean | $C_{10}$ | $C_{50}$ | $C_{90}$ | DR |
| Ex. 24 | None | — | 3 to 15 C. | 7.6 | 1.6 | 5.2 | 16.0 | 10.0 |
| Ex. 25 | Gelatin | 1% | 3 to 15 C. | 6.0 | 1.4 | 4.1 | 12.0 | 8.6 |

It may be seen from Table 4 that recrystallization of the KE agent employing a water/methanol mixture as the precipitation medium, with moderate external cooling to maintain a temperature above freezing but below room temperature throughout, yields particles having a surprisingly small mean size and a low DR, indicating a narrow size spread. Also surprisingly, the gelatin additive further reduced the mean particle size when added to the water/methanol mix at a concentration of about 1% and reduced the already low DR.

EXAMPLE 26

Crystallization of KE Agent in Methanol without Temperature Control

Example 24 is repeated using methanol as the sole precipitation medium component in place of the water-methanol mixture without external cooling. Some results obtainable are described in Table 5 below.

EXAMPLE 27

Crystallization of KE Agent in Methanol without Temperature Control, Using Nitrocellulose Precipitation Agent Example 26 is repeated employing a concentration of 0.1 percent by weight of nitrocellulose as a precipitation additive. Some results obtainable with Examples 26–27 are also described in Table 5 below.

TABLE 5

Recrystallization of KE agent using Nitrocellulose in Methanol as Precipitation Medium

| Experiment | Restrainer Type | Restrainer Conc. | Temperature Range ° C. | Slurry Particle Size (microns) Mean | $C_{10}$ | $C_{50}$ | $C_{90}$ | DR |
|---|---|---|---|---|---|---|---|---|
| Ex. 26 | None | — | 12 to 48 C. | 15.6 | 2.5 | 10.3 | 34.6 | 13.8 |
| Ex. 27 | NC | 0.1% | 12 to 46 C. | 35.1 | 2.7 | 14.6 | 74.9 | 27.7 |

It may be seen from Table 5 that nitrocellulose increased the crystal particle size when added to methanol at 0.1 percent by weight in a precipitation where no external cooling was used to control temperature. This result may be compared with above-described precipitations where use of external cooling to control temperature with 0.1% nitrocellulose decreases the crystal particle size.

From the foregoing description it may be seen that the invention can, in useful embodiments, provide economical methods and processes of preparing precipitated acetylenic agents having narrow ranges of desirably small particle sizes which can function consistently in TTI and other useful condition monitoring systems and are suitable for mass production. Such useful embodiments of the invention can also provide products incorporating the novel acetylenic agents produced by the method of the invention which comprise effective and economical shelf life systems and which provide opportunities for savings in time and material resources during system formulation.

Useful commercial products which can beneficially employ acetylenic agents made by the processes of the invention include the products referenced hereinabove, particularly but not exclusively in the background section of this specification, and other suitable products as will be apparent to those skilled in the art. One exemplary such product is a "TTI", a time-temperature indicator which provides a visual change so as a to indicate an environmental temperature exposure that is cumulative with time. The change may be a color change and may be embodied as a distinctive area in a printed label or tag, adjacent to which a reference marker is provided to facilitate reading of the indicative visual change. As referenced above such TTIs are useful for indicating the freshness of temperature-sensitive perishable products such as foodstuffs and vaccines.

Another such useful product comprises a radiation monitor for monitoring exposure to biologically damaging radiation, including, without limitation, actinic radiation, nuclear radiation, alpha, beta, or gamma radiation, electron beam radiation or the like. Desirably the radiation monitor comprises a radiation-sensitive tag or marker formulated with an active acetylenic agent which is selected or designed, according to the radiation to be monitored, to provide a visually perceptible change, e.g. a color change, indicative of a safe or other desired limit of radiation exposure. Optionally, a reference area can be provided adjacent the radiation-sensitive marker to facilitate reading of the marker.

It is anticipated that other embodiments and variations of the present invention will become readily apparent to the skilled artisan in the light of the foregoing description and examples, and such embodiments and variations are intended to likewise be included within the scope of the invention which is defined in the appended claims.

What is claimed is:

1. A process for recovering an acetylenic agent from solution, the process comprising:
   a) precipitating the acetylenic active agent by mixing a warm solution of the acetylenic agent with a cold precipitation fluid to precipitate particles of the acetylenic agent from the resultant mixture;
   b) controlling at least one size parameter of the precipitated acetylenic agent by selection of at least one constituent of the cold precipitation fluid; and
   c) collecting the precipitated acetylenic agent.

2. A process according to claim 1 comprising preparing the acetylenic agent solution by dissolving solid crystals or powdered acetylenic agent in a suitable solvent, by reconstituting a cake, slurry or other semi-solid mass or concentrate of acetylenic agent in the solvent, or by synthesizing the acetylenic agent in situ in the solvent.

3. A process according to claim 2 wherein the constituent selection comprises selecting a solvent to be employed as the precipitation fluid.

4. A process according to claim 2 wherein the constituent selection comprises selecting a solvent-soluble or -dispersible precipitation additive and incorporating the precipitation additive in the precipitation fluid.

5. A process according to claim 2 comprising selection of the solvent, selection of the precipitation additive and, optionally, of the additive's concentration to promote the obtaining of one or more desired size characteristics.

6. A process according to claim 2 wherein the size parameter controlled is that the acetylenic agent particles are desirably small or are substantially free of particles of a specified size greater than the mean particle size.

7. A process according to claim 2 wherein the controlling of the at least one size parameter of the precipitated acetylenic agent comprises managing the temperatures of the acetylenic agent solution and the recrystallization mixture to facilitate production of acetylenic crystals having a desirable size parameter.

8. A process according to claim 1, being a recrystallization process, the process comprising preparing the solution of acetylenic agent by dissolving crystals of the acetylenic agent in a suitable solvent.

9. A process according to claim 1 wherein the precipitation medium employed for quenching the hot acetylenic agent solution is chosen to be substantially a non-solvent for the acetylenic agent at the temperatures encountered during the crystallization process and to be miscible with the acetylenic agent solution.

10. A process according to claim 1 wherein the precipitation liquid comprises a nonmethanolic liquid selected from the group consisting of: ethyl 3-ethoxypropionate; dimethyl formamide; liquids comprising a maximum of 50 percent by weight methanol; aqueous liquids comprising a maximum of 30 percent by weight methanol; aqueous mixtures of lower C2–C6 alkanols; mixtures of ethanol, propanol or butanol with from about 30 to about 90 percent by weight water; petroleum ethers and distillates; heptane; hexane; and mixtures of two or more of the foregoing liquids.

11. A process according to claim 4 wherein the precipitation additive is used in a proportion of from about 0.001% to about 2% by weight of the precipitation medium or in a proportion of from about 0.005 to about 0.5% by weight of the precipitation medium.

12. A process according to claim 4 wherein the precipitation additive is soluble or dispersible in the precipitation medium to provide a solution or a dispersion or a colloidal dispersion, optionally in a proportion of from about 0.01% to 1.1% by weight of the precipitation medium.

13. A process according to claim 4 wherein the precipitation additive is effective to control a size parameter of the crystallizing acetylenic agent by limiting generation of overly large crystals, as is further described herein.

14. A process according to claim 4 wherein the precipitation additive comprises a cellulosic compound selected from the group consisting of cellulosic esters; cellulose ethers, optionally containing electronegative groups; methyl-, ethyl-, and carboxymethylcellulose; cellulose acetate butyrate; cellulose acetate propionate; cellulose acetate butyrate and nitrocellulose.

15. A process according to claim 4 wherein the precipitation additive comprises a compound selected from the group consisting of: gelatin; substituted polyethylene glycol polymers; surfactants; and substances capable of wetting the surfaces of the nascent crystals under the process conditions.

16. A process according to claim 1 comprising cooling the hot acetylenic agent solution by unassisted cooling to room temperature, by use of an ice bath, a dry ice bath or a programmable computer-controlled chiller.

17. A process according to claim 1 comprising cooling the hot acetylenic agent solution to a temperature range selected from the group consisting of: from about 40 to about −35° C., from about −25 to about −15° C.; from about 0 to about 5° C.; from about 3 to about 15° C.; from about 12 to about 48° C.; and from about 24 or room temperature to about 60° C., the temperature range being maintained during the crystallization.

18. A process according to claim 1 comprising cooling the hot acetylenic agent solution to a cooler temperature at least about 35° C. below the nominal acetylenic agent recrystallization temperature for the solvent, maintaining said cooler temperature at least about 35° C. below the nominal acetylenic agent recrystallization temperature throughout the crystallization process and optionally, maintaining the cooler temperature within a narrow range, for example within a range of about 10 to 15° C. throughout the crystallization process.

19. A process according to claim 1 wherein said acetylenic agent compound is selected from the group consisting of 2,4-hexadiyn-1,6-bis (ethylurea), 2,4-hexadiyn-1,6-bis (propylurea), a co-crystallization mixture of 2,4-hexadiyn-1,6-bis (ethylurea) and 2,4-hexadiyn-1,6-bis (propylurea), and a co-crystallized mixture of asymmetric synthesis comprising 2,4-hexadiyn-1-ethylurea-6-propylurea.

20. A process according to claim 1 wherein said acetylenic agent compound is selected from the group consisting of ethyl-, propyl-, butyl-, octyl-, dodecyl- and octyldecyl-substituted 2,4-hexadiyn-1,6-bis(alkylurea) compounds, the foregoing compounds wherein the alkyl substituents are linear, co-crystallized mixtures of any two or more of the foregoing compounds wherein the alkyl substituents are linear and co-crystallized mixtures of any two or more of the foregoing monomer components.

21. A process according to claim 1 wherein the acetylenic agent is dissolved in glacial acetic acid, dimethyl formamide, an alkyl ester of a monocarboxylic acid, a higher alkyl alcohol containing more than one carbon atom, an alkylated benzene, a cyclic ether, an alkyl ketone, an alkyl glycol ether, a halogenated alkyl hydrocarbon, ethyl acetate, methyl propionate, ethanol, butanol, isopropanol, toluene, xylene, trimethylbenzene, isopropylether, 1,2-dimethoxyethane, tetrahydrofuran, dioxane, acetone, methylethyl ketone, chloroform, dichloromethane, dimethyl sulfoxide, pyridine or a mixture of any two or more of the foregoing solvents.

22. A process according to claim 1 wherein:
a) the acetylenic agent is 2,4-hexadiyn-1,6-bis (ethylurea);
b) the precipitation medium comprises a solution of nitrocellulose in methanol; and
c) the precipitation mixture is maintained at a temperature of from about 0° C. to about 15° C. throughout the crystallization.

23. A process according to claim 1 wherein:
a) the acetylenic agent is 2,4-hexadiyn-1,6-bis (ethylurea);
b) the precipitation medium comprises a solution of about 0.05% to 0.10% nitrocellulose in methanol; and
c) the precipitation mixture is maintained at a temperature of from about −25° C. to about −15° C. throughout the crystallization.

24. A process according to claim 1 wherein:
a) the acetylenic agent is a 2:1 co-crystallization of 2,4-hexadiyn-1,6-bis (ethylurea) and 2,4-hexadiyn-1,6-bis (propylurea);
b) the precipitation medium comprises a solution of from about 0.01% to 0.10% nitrocellulose in methanol; and
c) the precipitation mixture is maintained at a temperature of from about 40° C. to about −35° C.

25. A process according to claim 1 wherein:
a) the acetylenic agent is a 2:1 co-crystallization of 2,4-hexadiyn-1,6-bis (ethylurea) and 2,4-hexadiyn-1,6-bis (propylurea);
b) the precipitation medium comprises a solution of from about 0.01% to about 0.5% nitrocellulose in ethyl 3-ethoxypropionate; and
c) the precipitation mixture is maintained at a temperature of from about 0° C. to about 10° C. throughout the crystallization.

26. A process according to claim 1 wherein the precipitation fluid comprises an aqueous methanol mixture comprising at least about 50% by weight water and at least about 10 percent by weight methanol.

27. A process according to claim 4 wherein the precipitation additive comprises from about 0.01 to about 1% by weight gelatin.

28. A process according to claim 1 comprising controlling the temperature of the precipitation mixture to promote formation of precipitate particles with a desired size parameter and optionally for ease of commercial implementation.

29. A process according to claim 1 wherein the acetylenic agent precipitate is largely or entirely crystalline.

* * * * *